US008753029B2

(12) United States Patent
Diamond

(10) Patent No.: US 8,753,029 B2
(45) Date of Patent: Jun. 17, 2014

(54) SYSTEM AND METHODS FOR SMOOTHLY INVERTING ONE OR MORE FACES OF A CUBICAL DEVICE

(75) Inventor: Solomon G. Diamond, Hanover, NH (US)

(73) Assignee: The Trustees of Dartmouth College, Hanover, NH (US)

( * ) Notice: Subject to any disclaimer, the term of this patent is extended or adjusted under 35 U.S.C. 154(b) by 457 days.

(21) Appl. No.: 13/126,858

(22) PCT Filed: Oct. 29, 2009

(86) PCT No.: PCT/US2009/062578
§ 371 (c)(1),
(2), (4) Date: Jul. 22, 2011

(87) PCT Pub. No.: WO2010/096118
PCT Pub. Date: Aug. 26, 2010

(65) Prior Publication Data
US 2011/0278417 A1    Nov. 17, 2011

Related U.S. Application Data

(60) Provisional application No. 61/109,441, filed on Oct. 29, 2008.

(51) Int. Cl.
*F16D 1/12*    (2006.01)

(52) U.S. Cl.
USPC .......................... 403/53; 248/349.1; 403/345

(58) Field of Classification Search
USPC .......... 248/349, 1, 274.1, 276.1; 403/53, 345; 74/417; 323/906
See application file for complete search history.

(56) References Cited

U.S. PATENT DOCUMENTS

2007/0281579 A1*  12/2007  Sambenedetto ............... 446/124
2012/0061968 A1*   3/2012  Burrell ............................ 290/55

* cited by examiner

*Primary Examiner* — Todd M Epps
(74) *Attorney, Agent, or Firm* — Lathrop & Gage LLP

(57) ABSTRACT

A system and method for inverting a cubical device 100 that inverts one or more faces of the cubical device 100 in a single fluid motion. In an embodiment, the cube faces are split in two face piece assemblies 210, in an alternative embodiment faces have only one invertible section 802, 702. The face piece assemblies 210 are initially held by cubical device 100 with a particular side facing inward. Operating the cubical device 100 causes one or more face piece assemblies 210, 803 to expand out from the center point of the cubical device 100, to rotate, and then collapse inward until cubical device 100 is reformed with the particular side of the faces in an outward-facing orientation. The joints, links and gears in the mechanism restrict the degrees of freedom to one such that the entire inversion movement is coupled. Multiple applications are proposed for the device, and embodiments having actuators for driving the inversion are disclosed.

20 Claims, 14 Drawing Sheets

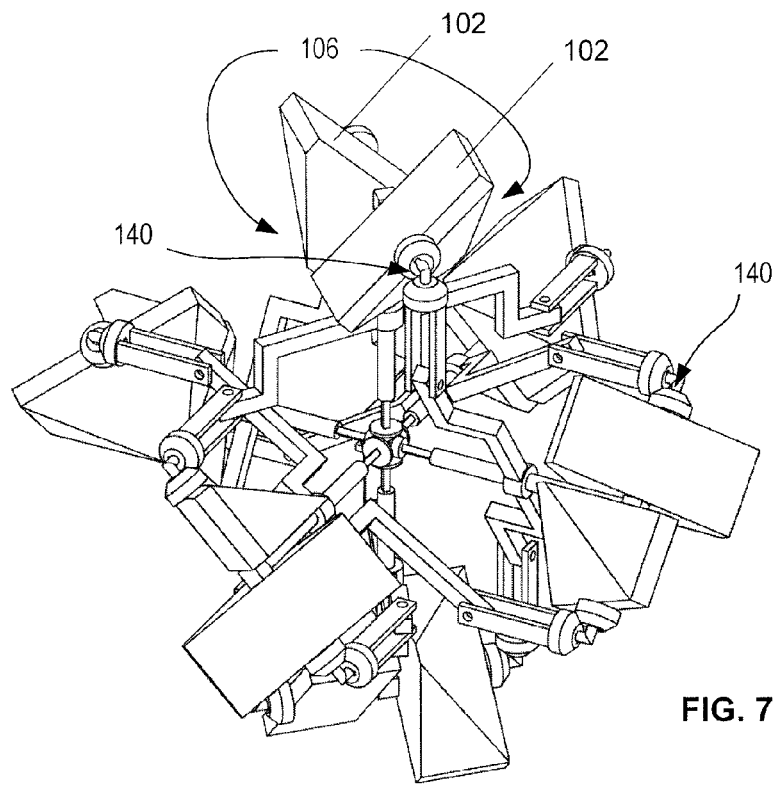
FIG. 7
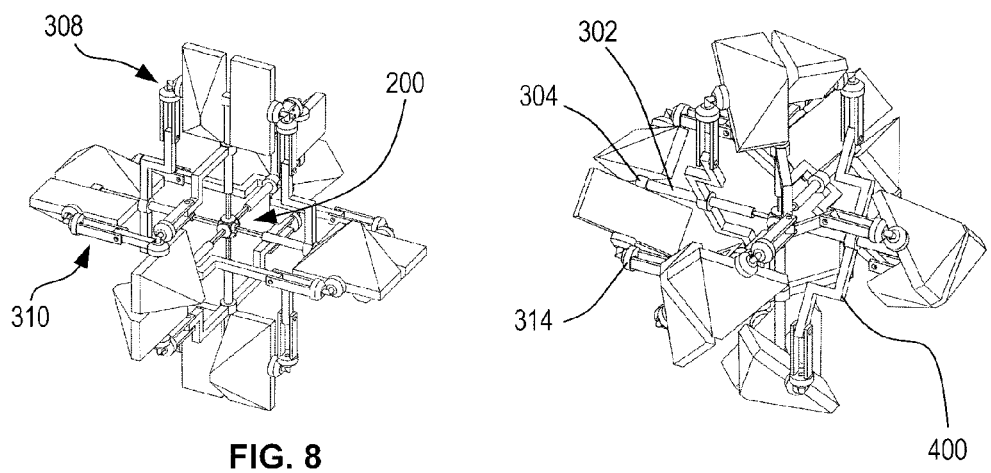
FIG. 8
FIG. 9

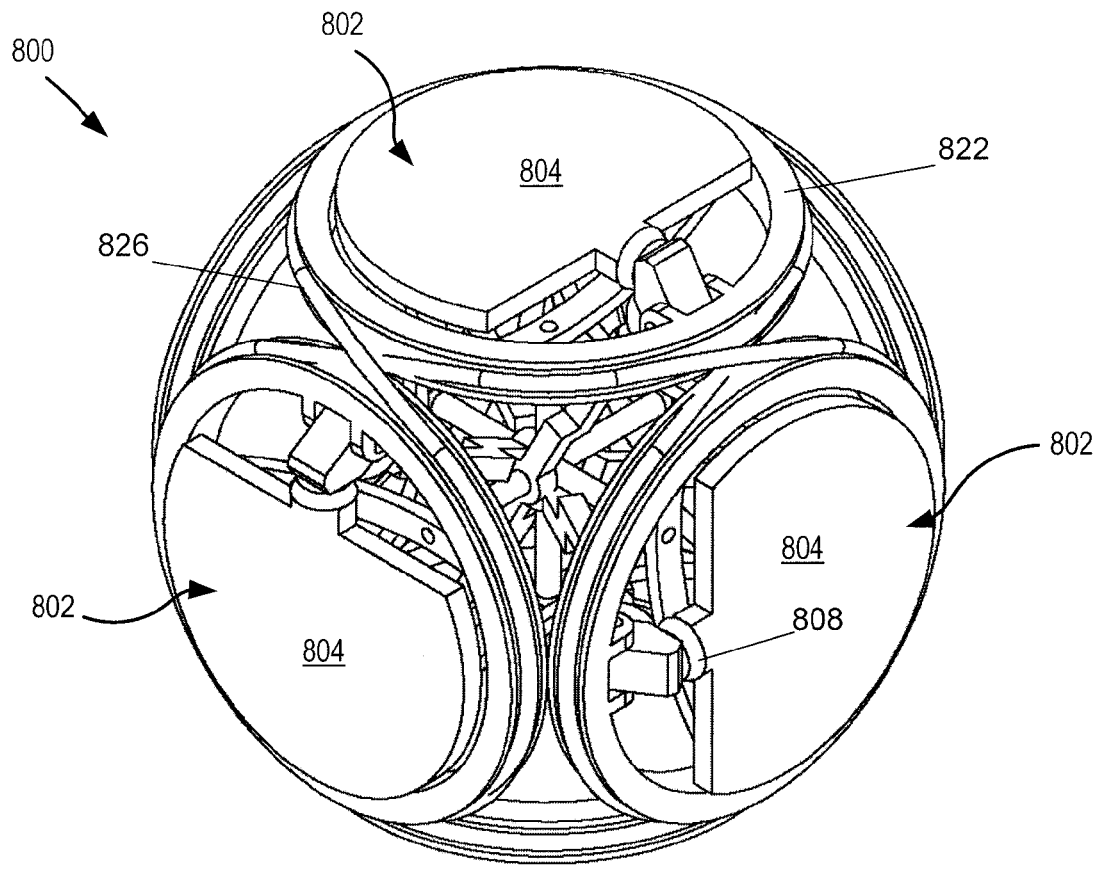
FIG. 20
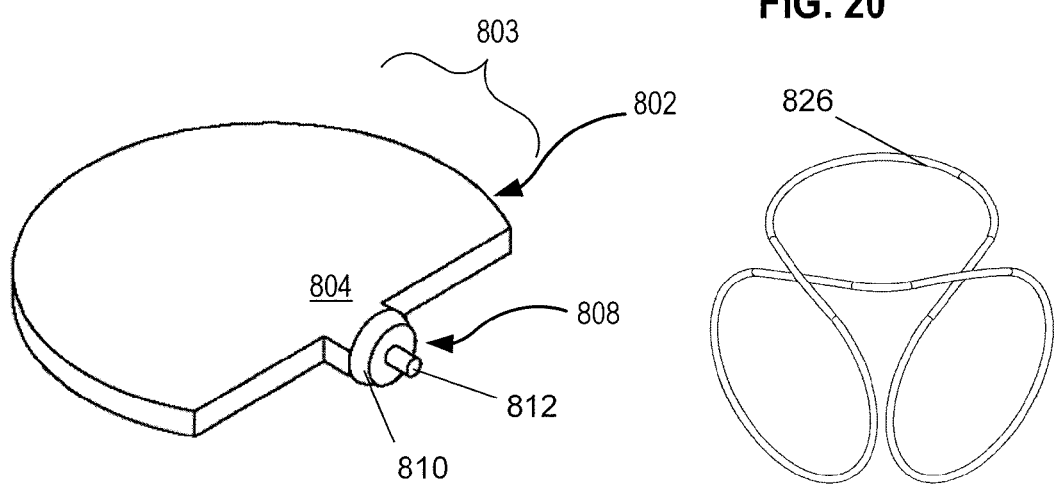
FIG. 22
FIG. 23

SYSTEM AND METHODS FOR SMOOTHLY INVERTING ONE OR MORE FACES OF A CUBICAL DEVICE

FIELD OF THE INVENTION

The present invention relates generally to a structure that inverts the faces of a device in a single fluid motion, the device, for example, has applicability in medical, satellite, and military technologies and as a toy or puzzle.

More specifically, the present invention is a cubical device, or fraction thereof, having one degree of freedom, with movements of all joints, links, and gears coupled, such that the device is capable of inverting its faces.

BACKGROUND

There are occasional applications for a device having two interchangeable outer surfaces, the outer surfaces being interchangeable, where the interchange of surfaces is powered either manually or under power from an actuator.

Application for such a device may include toys, satellites or other devices having delicate equipment fixed to one of the two interchangeable outer surfaces. For example, a solar collector may have one side exposed for power collection and another side exposed during hailstorms. Similarly, a satellite may protect its solar arrays by exposing a bare surface until launch, after which the exterior surface inverts to expose the solar arrays.

Another application may include weather/climate dependent camouflage for remote sensors placed in cold-weather climates. Such a remote sensor may have need to interchange a green, brown, or mottled green-brown exterior with a white exterior during or after a winter storm to avoid visual detection. Other applications are also possible, including some discussed below.

SUMMARY

A device 100, in an embodiment roughly cubical, has at least two faces. The device is capable of inverting the faces.

In an embodiment, the device has a hub assembly 200 having multiple axis arms 204 and multiple face axle assemblies 300. Each face axle assembly has a face axle 306 and is slidably engaged with an axis arm 204 of the hub assembly 200. The device also has multiple rotating arm assemblies 400, each rotating arm assembly 400 being engaged with a face axle assembly 300. Each face axle assembly has at least one face piece assembly 210 coupled to it, and to two rotating arm assemblies 400, and each face piece assembly 210 is rotationally engaged with one face axle assembly 300. The hub assembly 200, face axle assemblies 300, rotating arm assemblies 400, and face piece assemblies 210 are cooperatively configured to extend face pieces 102, 702, 802 outwardly from the device 100, to invert the face pieces 102, 702, 802, and to retract the face pieces 102, 728, 802.

Another embodiment has a ring 822 associated therewith, and coupled to through a link, a face piece 802 assembly 803. Face piece assembly has a beveled driving wheel 808 as well as a face piece. A wheel 814 is attached to the link and drives the beveled driving wheel 808; a rotating arm 818 is also rotationally coupled to the driving wheel. The face piece assembly 803 is coupled to the link in manner such that face piece assembly 803 may rotate relative to the link. Rotation of the ring 822 causes rotating arm 818 to rotate thereby causing rotating arm 818 to deflect link 820 thereby deflecting face piece assembly 803 away from the device to give clearance, and causing rotating arm 818 to rotate wheel 814 thereby rotating face piece assembly 803.

An inverting cubical device is assembled from a hub assembly, six hinge arm assemblies, six rotating arm assemblies, and a plurality of face piece assemblies. The movement of the hub assembly, hinge atm assemblies, rotating arm assemblies, and face pieces assemblies are coupled. The device is capable of movement to expand the cube, invert the face pieces, and contract the cube in one fluid motion.

Alternative embodiments proposed have angular and curved as well as flat faces. Another embodiment has suture needles attached to a face; this embodiment can link to skin and to other adjacent devices to form a bandage. Still other embodiments are of use in camouflage applications.

BRIEF DESCRIPTION OF THE FIGURES

FIGS. 7, 8, and 9 illustrate intermediate stages of the device of FIG. 1 as it is inverted to the form of FIG. 6.

FIG. 20 is a perspective view of an embodiment of the cubical device having face pieces that elevate, and then rotate to invert.

FIG. 22 is an illustration of a single face piece of the embodiment of FIG. 20 with its attached beveled driving wheel.

FIG. 23 is an illustration of a belt that may be used in an embodiment to couple inversion of multiple sides of the embodiment of FIG. 20.

DETAILED DESCRIPTION OF THE EMBODIMENTS

Figure 1:
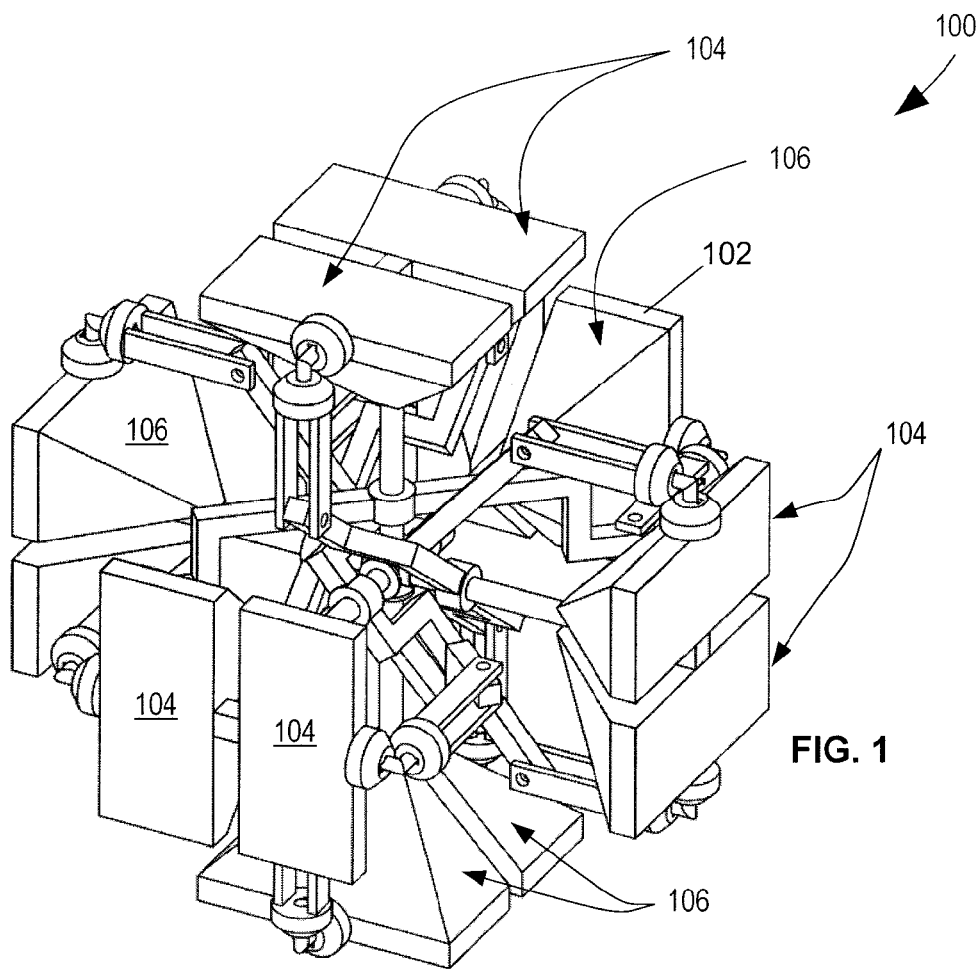
FIG. 1 is a perspective view of an embodiment having two-piece faces in a cubical arrangement.
Figure 6:
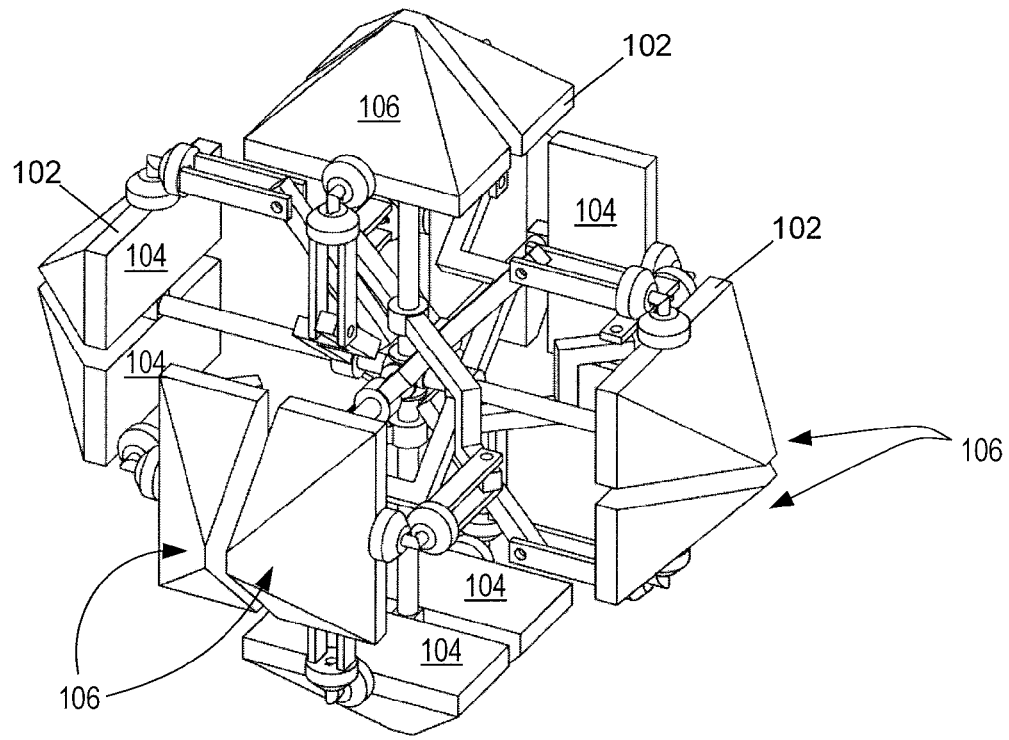
FIG. 6 illustrates in a perspective view a completed inversion of the embodiment of FIG. 1.

FIG. 1 illustrates an embodiment of an inverting cubical system or device 100. The inverting cubical system or device 100 has the property that it has face pieces, such as face half sections 102 that can reversibly invert. When these face half section invert, they transition from having a first side, such as side 104 on an exterior of the device 100 to having a second side, such as side 106, facing on an exterior of the device, with the first side 104 facing an interior of the device. A completed inversion of the device 100 of FIG. 1 is illustrated in FIG. 6.

FIG. 1 illustrates an embodiment having two face half sections, such as face half sections 102, on each face of the device 100. Each of face half sections 102 has two or more opposed faces. In an embodiment, illustrated in FIGS. 1 and 2, the two opposed half faces 102 include a flat face 104 and an angular face 106. In an embodiment, as further detailed in FIG. 10, angular face 106 has two right triangular surfaces each connected to two isosceles trapezoidal faces.

Embodiments having other configurations of faces and of face pieces are possible, and may better serve in different applications for the device 100. The face piece 108 of FIG. 3, for example, has a flat face 110 and a curved face 112. Embodiments having face pieces similar to that of FIG. 3 may, for example, have an ability to roll like a ball when curved faces 112 are presented on the exterior of the device, while being unable to roll when curved faces 112 are facing an interior of the device and flat faces 110 are facing the exterior of the device.

Figure 4:
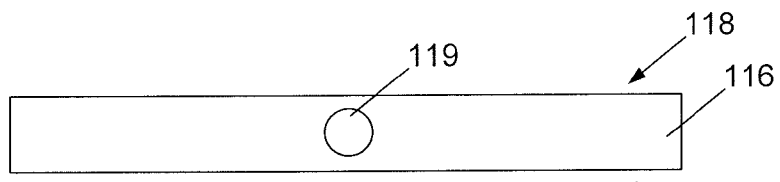
FIG. 4 is a side view of a face piece having two flat sides.

The face piece or face half section 116 illustrated in FIG. 4 has two flat faces, 118 and 120. While these are both topologically flat, they may differ in other ways. For example, face 118 may be painted dark green, and face 120 may be painted white. Such a device may be inverted to change its apparent color from dark green to white, or from white to green, as needed to camouflage its appearance.

Figure 3:
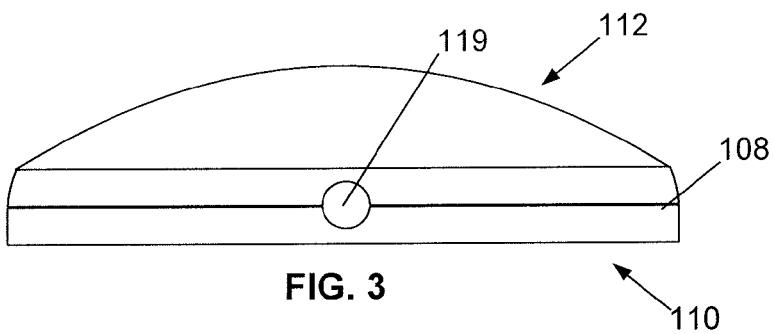
FIG. 3 is a side view of a face piece having a flat and a curved side.
Figure 2:
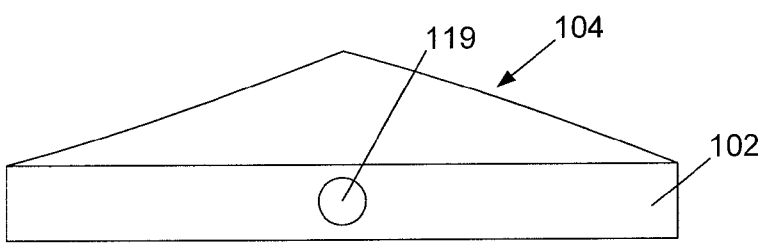
FIG. 2 is a side view of a face piece having one angular and one flat side.

Each face piece or face half section as illustrated in FIG. 2, 3, or 4 has a central axle hole 119.

Figure 5:
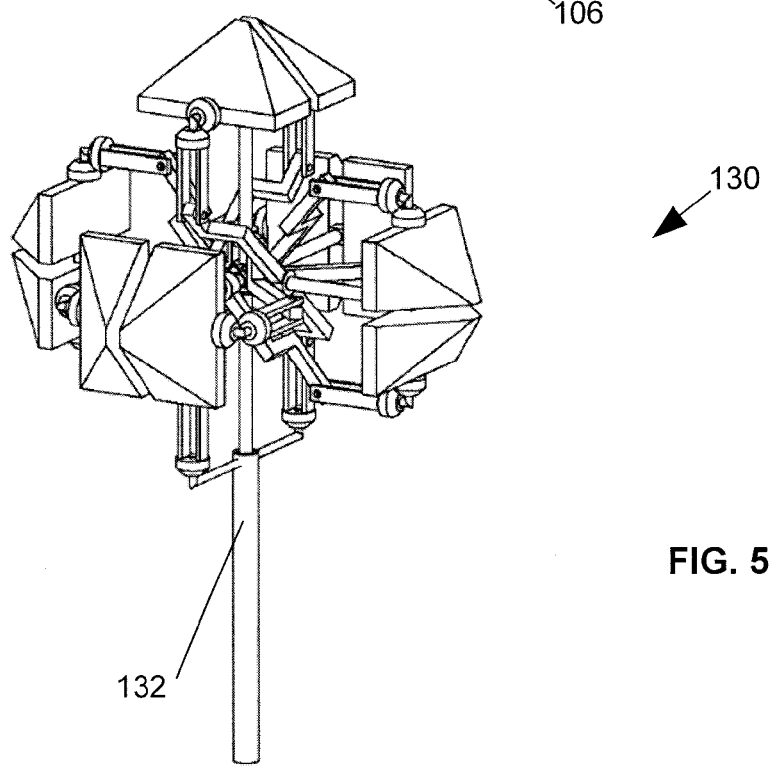
FIG. 5 is a perspective view of an embodiment having only 5 faces and mounted on a rod.

The embodiment 130 of FIG. 5 has face half sections 102 of one side either removed as shown, or replaced with narrower face pieces, as necessary to fit in a larger system and/or to clear a mounting device. The embodiment 130 of FIG. 5 has a mounting device having a support rod 132 for mounting the device 130 to a stake, or for attaching the device to a larger system. The embodiment 130 of FIG. 5 is otherwise similar to that of FIG. 1.

A stake-mounted variation on the embodiment of FIG. 5 may have faces having a winter camouflage pattern on one side, and a summer camouflage pattern on the other side, such that it may reversibly transform from winter to summer camouflage to avoid detection as snow falls, and as snow melts, in an environment where snow typically melts quickly between storms. Such a device may have sensors and a broad-spectrum radio transmitter within it, such that it may serve as a remote sensing device planted near a trail for monitoring civilian and insurgent traffic on the trail. Sensors of such a device may include cameras and ground vibration sensors.

Yet another embodiment of the device may have four solid sides coated with a rough, dull-finished, ceramic patterned to resemble a rock. Invertible face pieces of a top of the device have a similar rough, dull, finish on one side, and a solar cell for recharging batteries of the device on the other. This embodiment has sensors and a broad-spectrum radio transmitter within it, such that it may serve as a remote sensing device planted near a trail for monitoring civilian and insurgent traffic on the trail. The device presents the solar cell of the face pieces outwards when no movement is detected in the area for recharging, thereby providing a longer service life than available with non-rechargeable batteries, but when vibrations or movement is detected it presents the rough dull finish side of the face pieces for optimum concealment.

Figure 19:
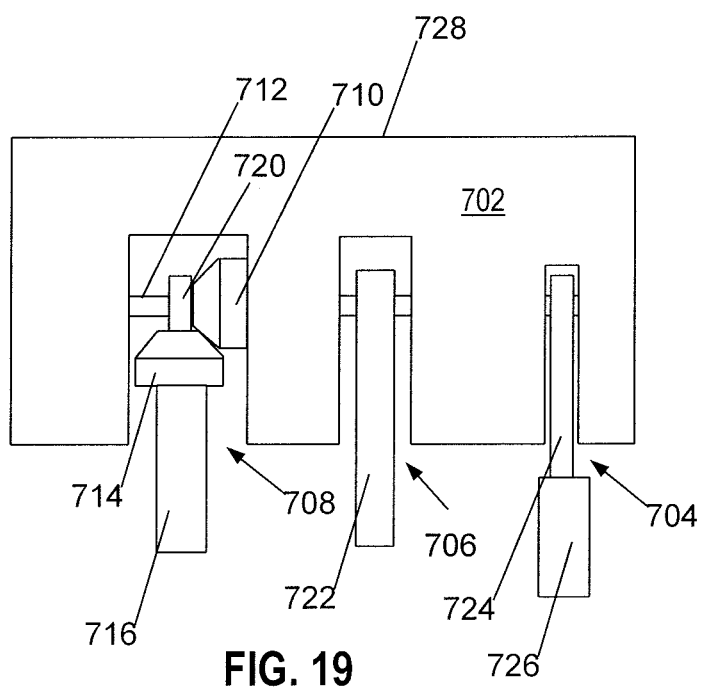
FIG. 19 is a view of a face piece with adjacent components of an embodiment having a single, enlarged, face piece per side of the cubical device.

In the embodiments of FIG. 1, paired face half sections 102, or solid face pieces as illustrated in FIG. 19, are attached to the device, and are manipulable through a mechanism that will be further detailed below.

Figure 27:
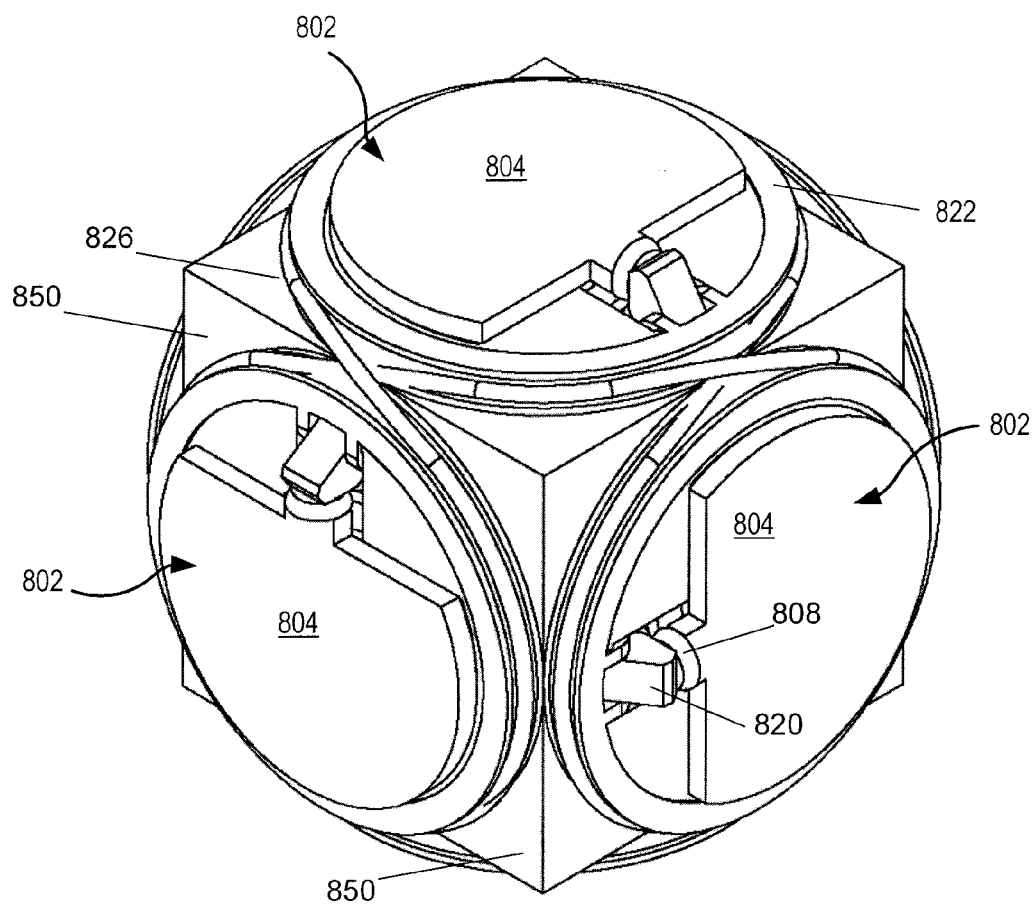
FIG. 27 is a view of a version of the device having a housing so it can be sealed.

Various embodiments of the device may have relatively open corners between face pieces as illustrated in FIG. 1, or relatively closed corners between face pieces. Other embodiments may have face pieces that meet in closer proximity than those illustrated. Other embodiments may have housing portions that close corners of the device, as illustrated in FIG. 27. In some embodiments, as illustrated in FIG. 19, face pieces or face half sections may have slots such that they may be larger and such that components of the mechanism may be protected when the device is in a closed position.

As previously noted, FIG. 6 illustrates a completed inversion of the embodiment of FIG. 1. In the FIG. 6 configuration of the embodiment, faces 106 that faced the interior of the device 100 as configured in FIG. 1 are facing the exterior of the device, and faces 104 that faced the exterior of the device as configured in FIG. 1 are facing the interior of the device.

In progressing from the configuration of FIG. 1 towards the configuration of FIG. 6, it is necessary to expand the device by extending the face pieces or face half sections 102 outwards so that they can be inverted with inward edges of the face pieces clearing the mechanism. FIG. 7 shows device 100 at a point partway through the expansion phase of the transformation. The expansion phase is characterized by outward movements of supporting axles 140. The face pieces or face piece half sections simultaneously rotate about the axles 140. In the embodiment of FIG. 1 and FIG. 2, the face piece half sections of each side rotate in opposite directions, however in an alternative embodiment resembling that of FIG. 19, face pieces 702 have only one section for each side of the device and therefore rotate as a unit for each side.

FIG. 8 shows device 100 at the completion of the expansion phase. FIG. 9 shows device 100 at a point half way through a contraction phase with an orientation of face half sections 102 with formerly-internal side 106 facing the exterior of the device. FIG. 6 shows device 100 at the completion of a contraction phase of transformation after supporting axles 140 move inwardly. The transformation process is reversible provided that any actuator that may be provided for driving the inversion mechanism is reversible.

In a toy embodiment of device 100, the cubical device may be constructed from thermoplastics, and the inversion is driven by an external driving force. An example of an external driving force is a person manipulating device 100 by hand.

In another embodiment, a driving force is provided by an actuator provided internal to device 100. In variations on this embodiment, the actuator may be an electric motor, a linear spring, a torsion spring, a piston, or a chemical gas generator with a piston and cylinder. Other internal and external actuators are possible, including hydraulic and pneumatic pistons and cylinders.

In an embodiment, the inversion mechanism of device 100 is fully coupled, allowing a single actuator to drive the inversion and to be placed internally to one or more components, or attached to many points within device 100. For example, the actuator may be a torsion spring, or an electric motor, within a face half section 102, or a linear spring or piston within or adjacent to sliding arm 302 (FIG. 11). Furthermore, the actuator may be attached to one or more of a hub assembly 200 (FIG. 14), a face axle assembly 300 (FIG. 11), a rotating arm assembly (FIG. 15), and one or more face piece assemblies 210 (FIG. 10).

The transformation, or inversion, of device 100 is understood to be the process of smoothly expanding the device 100, inverting the paired face piece assemblies 210, and contracting the device 100 in one fluid motion.

Figure 10:
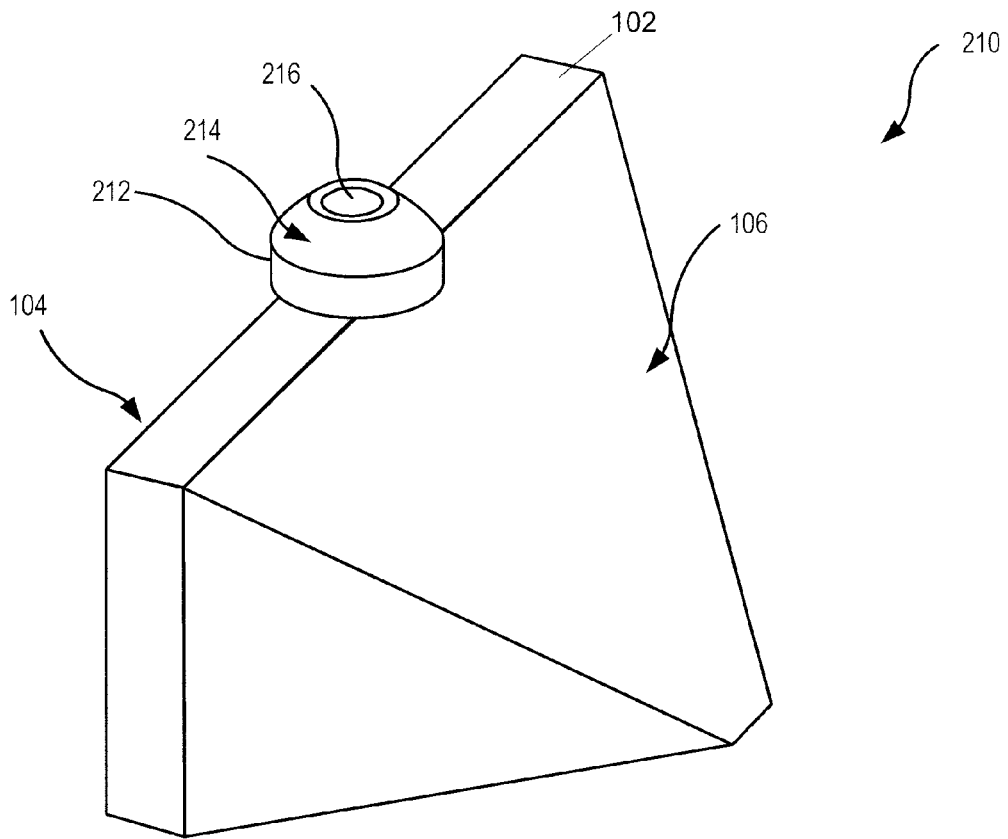
FIG. 10 is a perspective view of a face piece assembly in an embodiment similar to that of FIG. 1.
Figure 11:
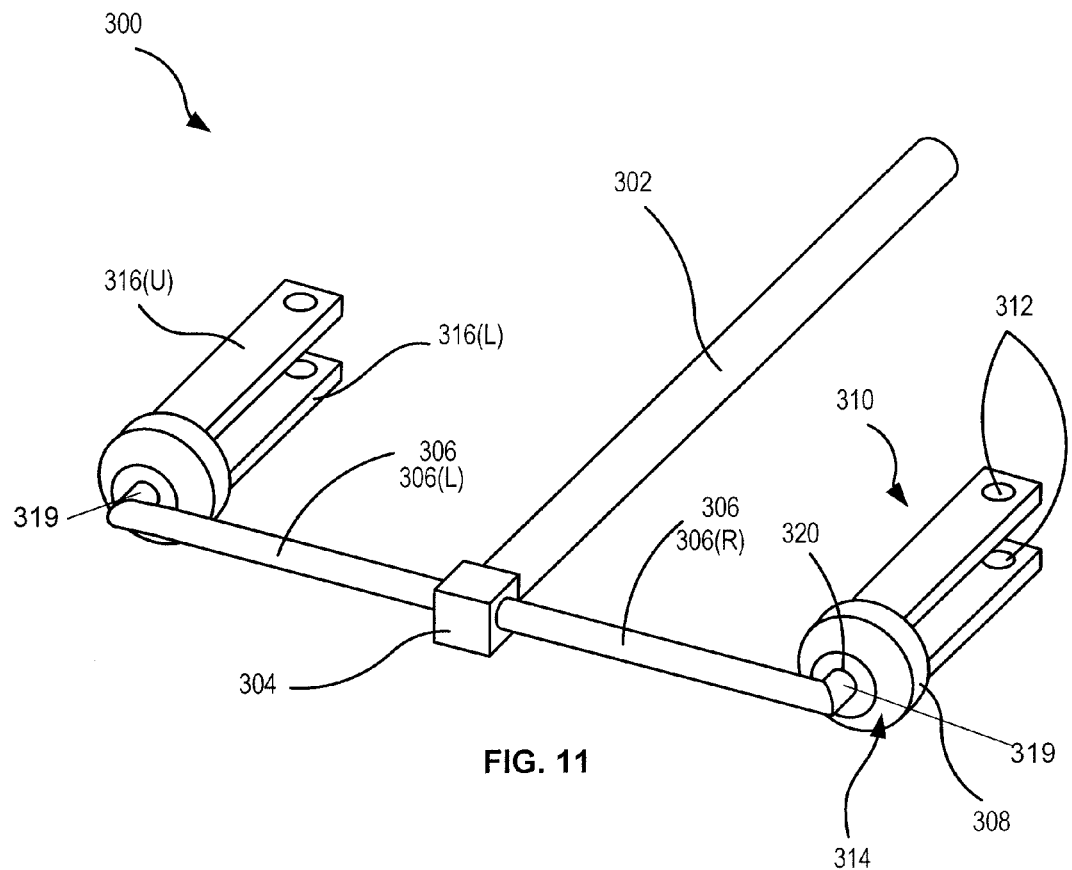
FIG. 11 is a perspective view of a face axle assembly and face axle, in an embodiment.

FIG. 10 shows one embodiment of a face piece assembly 210. Two face piece assemblies 210 together make up one of the six faces of the inverting cube, as depicted in FIG. 1. Face piece assembly 210 includes a face half section 102, 108, or 116 or face piece 702 as previously discussed with reference to FIG. 2, 3, 4, or 19. In an embodiment having flat and angular face half sections as illustrated, face half section 102 has flat face 104, an angular face 106, and a face pivot wheel 212.

Face pivot wheel (FPW) 212 has an FPW beveled face 214, and a face axle hole 216 aligned with axle hole 119 of any attached face piece or face half section 102. Face axle hole 216 may be equipped with a bearing. Beveled face 214 may be coated with a non-slip material such as rubber, may have a textured surface, or may be cut with beveled-gear teeth, to reduce or eliminate slipping when engaged with other components of the mechanism such as hinge pivot wheel 308 (FIG. 11). In a thermoplastic embodiment, face pivot wheel 212 may be cast into face piece or face half section 102; in other embodiments face pivot wheel may be welded, glued, or otherwise attached to face piece or face half section 102.

Face axle hole 216 (FIG. 10) accepts face axle 306 (FIG. 11) as to allow face piece assembly 210 to rotate unimpeded on face axle 306. Face axle 306 has a right-angled extension 319, which may be attached by welding, gluing, or threaded attachment after face piece assemblies 210 are placed over face axle 306.

A hinge pivot wheel 308 intermeshes with the beveled face of the FPW and drive the rotation of face piece assembly 210 (FIG. 11) about face axle 306 during the inversion process. The hinge pivot wheel (HPW) 308 has a beveled face 314 that is coated with a friction material in some embodiments, has a textured surface in other embodiments, and is cut with beveled gear teeth in other embodiments, as necessary to engage with the FPW. Hinge pivot wheel 308 is rotationally coupled to the face axle extension 319 such that it may rotate freely on the face axle extension.

Junction 304 is illustrated as cubical, but may have almost any shape. Junction 304 holds sliding arm 302 at a right angle to the face axle 306. In the illustrated embodiment, face axle 306 may be formed either of two parts or of a single shaft passing through junction 304, and provides left face axle 306(L) and right face axle 306(R), on opposite faces of junction 304.

Face axle 306 extensions 319 are rotatably attached to hinge pivot wheel 308. In one embodiment, face axle 306 is connected to hinge pivot wheel 308 via a rotating connector 320, as to allow hinge pivot wheel 308 to rotate freely about extension 319. Examples of rotating connector 320 include, but are not limited to, a ball and socket joint, a rotational bearing and a MicroElectroMechanical (MEMS) rotational bearing. Hinge pivot wheel 308 has a beveled face 314, located adjacent to rotating connector 320. The bevel angle of HPW beveled face 314 is complimentary to the bevel angle of Face Pivot Wheel (FPW) beveled face 214 (FIG. 10) as to engage therewith when the bevels are in contact. In an embodiment, the bevel angles of HPW beveled face 314 and FPW beveled face 214 are formed at 45 degrees. In one embodiment, each HPW beveled face 314 is in constant contact with a FPW beveled face 214 of a face pivot wheel 212. FPW beveled face 214 remains in frictional contact with HPW beveled face 314 as it rotates about HPW beveled face 314.

FIG. 11 shows an embodiment of a face axle assembly 300. Assembly 300 includes sliding arm 302, junction 304, face axle 306, hinge pivot wheel 308, hinge arm 310, and hinge arm holes 312. Sliding arm 302 is constructed with a hollow interior 301 (FIG. 12), with a single opening opposite connection junction 304. The hollow interior 301 (FIG. 12) is square in cross-section and of adequate length to engage the mating square cross-sectional shape of axis arm 204 (FIG. 13) throughout the transformation process.

Figure 13:
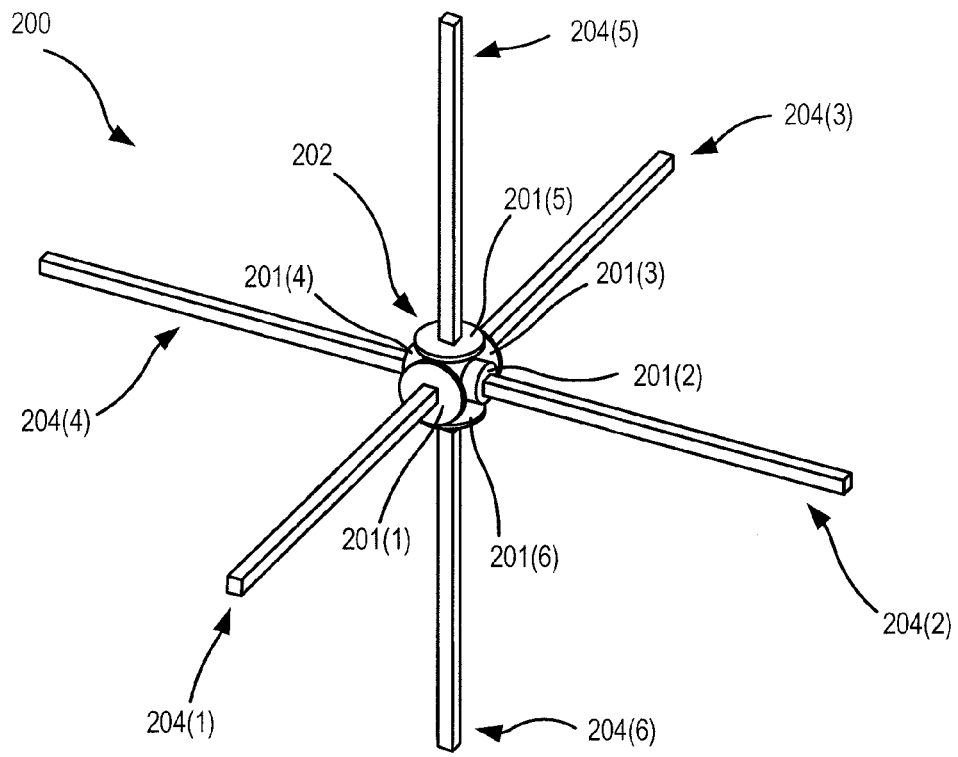
FIG. 13 is a perspective view of a hub assembly, in an embodiment.

Together a first face piece assembly 210 and second face piece assembly 210, each having a face half section 102, make up one face of device 100, as depicted in FIG. 1. As can be seen in the five transformation steps illustrated in FIGS. 1 and 6-9, in an embodiment having two face half sections, a first face piece assembly 102 and a second face piece assembly 102 rotate about face axle 306 in opposing directions FIG. 13 shows an embodiment of a hub assembly 200 for device 100. Hub assembly 200 includes a hub 202 and six axis shafts or arms 204 (1)-204(6). Hub 202 supports six beveled transmission wheels, hub beveled wheels 201(1)-201(6). In variations of this embodiment, hub beveled wheels 201(1)-201(6) may be beveled gears or beveled friction wheels. Each hub beveled wheel 201 is statically fixed to one of the six axis arms 204(1)-204(6). Hub beveled wheels 201 are rotationally fixed in hub 202. Each axis arm 204(1)-204(6) extends towards a separate face of the cubical device 100. Axis arm 204(1), axis arm 204(2), and axis arm 204(5) are all orthogonal to one another. All axis 204 are shown as square in cross section, but may be any cross sectional shape as to be mate with a sliding arm 302 (FIG. 11) of assembly 300 (FIG. 11) in a smooth, non-rotational, sliding configuration. Each axis arm 204 in statically fixed to a hub beveled wheel 201. Axis arm 204(1) is fixed to hub beveled wheel 201(1); axis arm 204(2) is fixed to hub beveled wheel 201(2), etc.

Since opposing sides of the device 100 are coupled through the rotating arms 400 (FIG. 16), only three hub beveled wheels 201 need be used to link, and synchronize inversion of, all sides of the device; in an embodiment three hub beveled wheels and three idler wheels are used.

In another embodiment of assembly 200, hub 202 may support electronics, mechanics, a reservoir, and a power supply. The electronics may monitor properties of the surrounding environment of device 100, to wirelessly transmit data, wirelessly receive commands, and control the actuator. An actuator may be integrated into device 100 to drive the transformation process of device 100. The reservoir may contain substances that can be released into the immediate environment of device 100. The power supply may power the electronics, mechanics, and reservoir.

Figure 14:
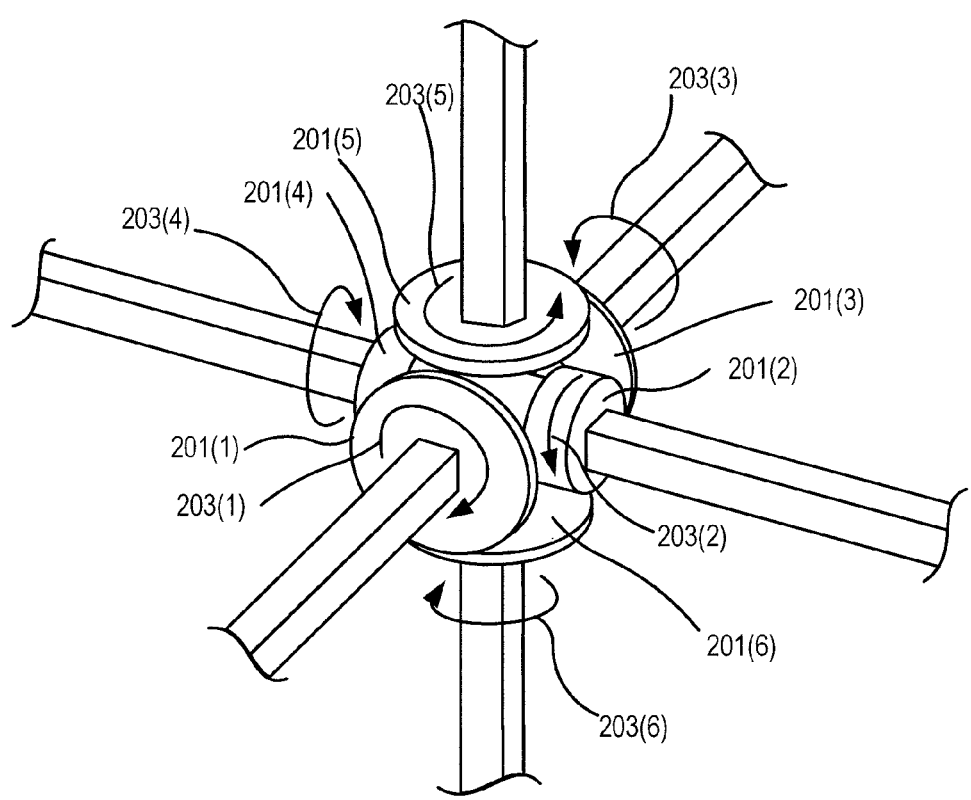
FIG. 14 shows one embodiment of the rotation directions of hub beveled wheels, in an embodiment.

FIG. 14 shows an embodiment of the hub 202 in more detail than visible in FIG. 13. FIG. 14 is annotated to show rotation directions of the hub beveled wheels 201. The rotation of beveled wheels 201(5) opposes that of 201(6), and the rotation of 201(1) opposes that of 201(3). Hub beveled wheels 201(5), 201(6), 201(1), and 201(3) intermesh with hub beveled wheels 201(2). Also, hub beveled wheels 201(5), 201(6), 201(1), and 201(3) intermesh with hub beveled wheels 201(4).

Since several of these beveled wheels 203(1)-203(6) are indirectly coupled to others of these beveled wheels via linkages elsewhere in the device 100, some of the beveled wheels at the hub may be replaced by idler wheels in a fully functional device.

Figure 12:
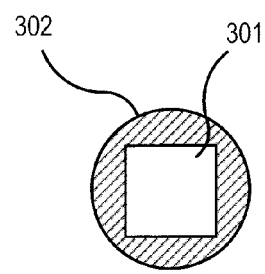
FIG. 12 shows a cross-sectional view of a sliding arm, in an embodiment.

With reference to FIGS. 11 and 12, Axis aims 204(1-6) slideably engage with the inner surface 301 of sliding arm 302. One sliding arm 302 and face axle 306 is provided for each axis arm 204(1-6). Hollow interior 301 may be of any cross-sectional shape as required to mate with any number of cross-sectional shapes of axis arm 204. In the illustrated embodiment, axis arm 204(1), of square cross sectional shape is fitted internally to hollow interior 301 of square cross sectional shape, as to restrict sliding arm 302 to movement along the length of axis arm 204(1) without rotation about axis arm 204(1). Sliding aim 302 and axis arm 204(1) remain engaged during inversion because axis arm 204(1) is longer than the travel of sliding arm 302 allowed by the one degree of freedom of movement of device 100.

Figure 16:
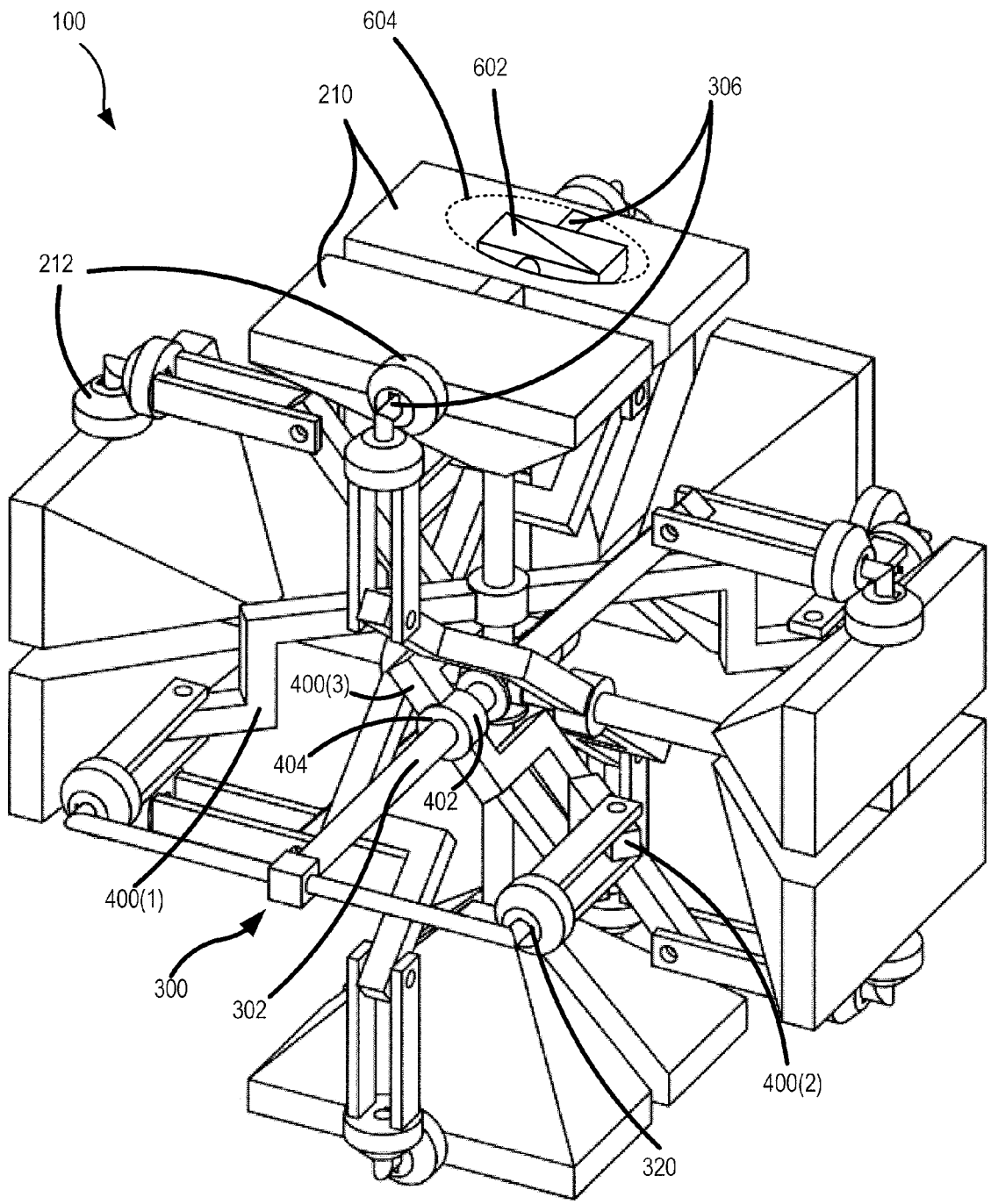
FIG. 16 is a perspective view of a flat face out system with the front face piece assemblies removed for clarity, in an embodiment.

FIG. 16 is a perspective view of the embodiment of FIG. 1 with a face removed to allow a better view of the mechanism for inverting the faces.

Figure 17:
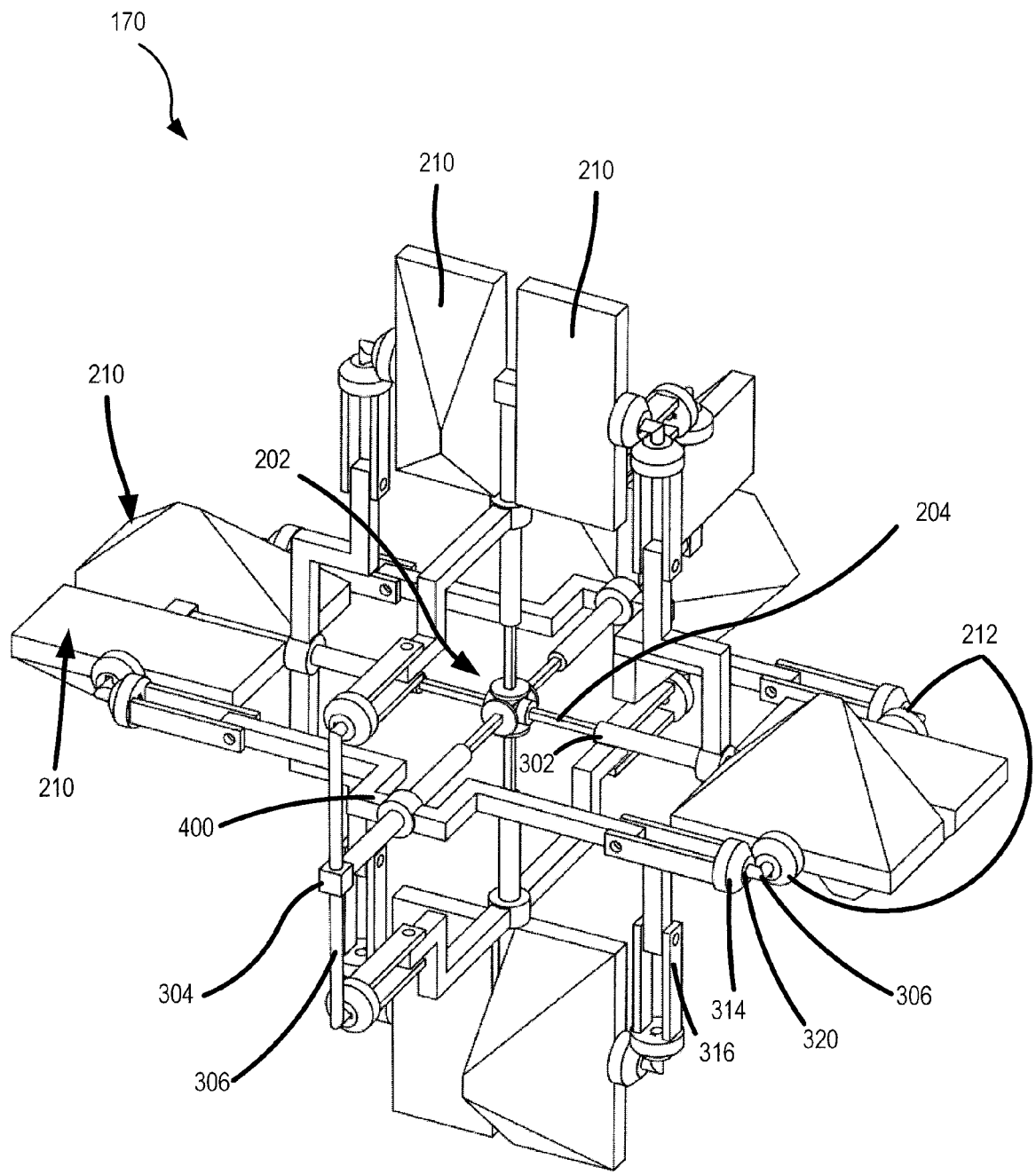
FIG. 17 is a perspective view of an expanded system with the front face piece assemblies removed for clarity, in an embodiment.

The cylindrical exterior of sliding arm 302 is rotatably and slideably engaged with rotating arm assembly 400 (FIG. 15) via pivot hole 404 as depicted in FIG. 16 and FIG. 17.

Referring to FIG. 11, the base of hinge pivot wheel 308 is attached to a hinge arm 310. Hinge arm 310 includes an upper hinge plate 316(U) and a lower hinge plate 316(L) spaced a distance apart. Both plate 316(U) and plate 316(L) have a hole, such as hinge arm hole 312, at the end farthest from the hinge pivot wheel 308. Hinge arm hole 312 accepts a pivot connector to rotationally secure stepped rotating arm 406 (FIG. 15) to hinge aim 310. Hinge arm hole 312 acts as pivot point for rotating arm assembly 400 relative to hinge aim 310. The separation distance of the plate 316(U) from the plate 316(L) is equal to or slightly larger than the thickness of a stepped rotating arm 406 (FIG. 10), as to allow unrestricted rotational movement of rotating arm assembly 400 (FIG. 10) about the point securing rotating arm assembly 400 to hinge arm 310.

Figure 15:
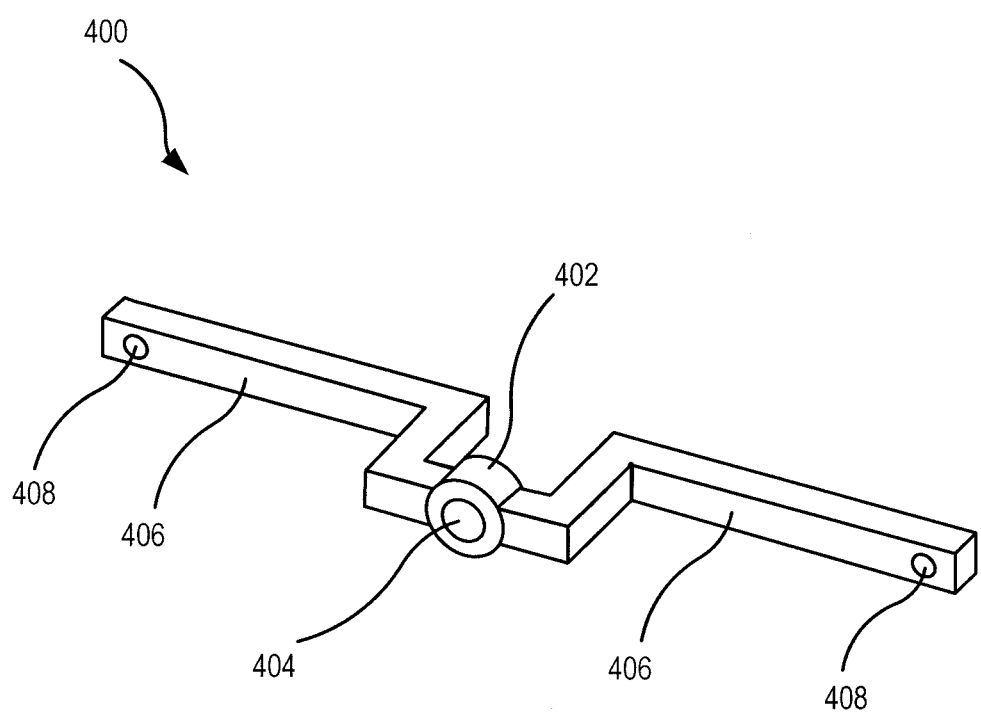
FIG. 15 is a perspective view of a rotating assembly, in an embodiment.

FIG. 15 shows one embodiment of a rotating arm assembly 400. In this embodiment, assembly 400 includes a central pivot 402 coaxially constructed with a pivot hole 404. Two stepped rotating arms 406 are integrated with pivot 402 at 180 degrees from each other. Rotating arms 406 have a pair of 90 degree angles as to form a stepped structure in rotating arms 406; the step permits the arms to clear the hub 202. Rotating arm holes 408 are located at the ends of the rotating aims 406. Pivot 402 may be slideably and rotatably engaged with sliding arm 302, via pivot hole 404, in such a way as to allow assembly 400 to smoothly travel along the cylindrical exterior surface of sliding arm 302, and rotate about the axis shared by sliding arm 302, pivot hole 404 and pivot 402, as depicted in FIG. 16. Holes 408 (FIG. 15) accept a pivot connector to rotationally secure stepped rotating arm 406 to hinge arm 310 (FIG. 11).

In a satellite embodiment, the cubical device may be constructed from carbon fiber, plastic, metal, metal foils, ceramic, or resin material as to ensure the device is light weight and durable. The inversion driving force is an actuator internal to device 100. In an embodiment, the internal actuator is an electric motor; in alternative embodiments the actuator is a linear or torsion spring, or a piston. The components of device 100 are coupled, allowing the actuator to be placed internally to one or more components, or attached to several alternative locations within device 100. An internal actuator may be an electric motor, a linear spring or a torsion spring placed internally to a face piece assembly 210 (FIG. 10), a sliding arm 302 (FIG. 11), or a chemical gas generator may actuate a piston placed internally to sliding arm 302. Furthermore, the actuator may also be attached to one or more hub beveled wheels 201 (FIG. 13) of hub assembly 200 (FIG. 13), a face axle assembly 300 (FIG. 11), a rotating arm assembly (FIG. 15), or one or more face piece assemblies 210 (FIG. 10). In one embodiment, the actuator is an electric motor 602 (FIG. 16) as seen through transparent surface 604 (FIG. 16).

In this embodiment, the initially exposed face may be a protective surface capable of withstanding launch and deployment from a vehicle. The face exposed after transformation may incorporate a large number of solar cells for optimum power production. In another embodiment, the initially exposed face may be a light colored or reflective surface for low solar heat absorption and good cooling, and the face exposed after transformation may be a darker, more absorbent, surface for solar absorption and heating. The transformation may be reversible with an appropriate actuator, providing opportunities to convert between the high solar reflectance to the high solar absorbance states for maintenance of proper temperature.

In an embodiment for a Robotic Actuated Suturing and Therapeutics for Emergency Response (RASTER), the device may be constructed from one or more of metal, silicone, plastic, ceramic, and resin materials. The dimensions of this embodiment may be on the centimeter to millimeter scale. Semiconductor device fabrication techniques may be employed in the manufacturing process. The inversion driving force is an actuator internal to device 100, and in an embodiment is a micro-motor. In alternative embodiments the actuator may be a linear or torsion spring, or a chemical actuator providing gas to drive a piston or cylinder as heretofore described. In alternative embodiments, the actuator is within a sliding arm 302 (FIG. 11).

Figure 18:
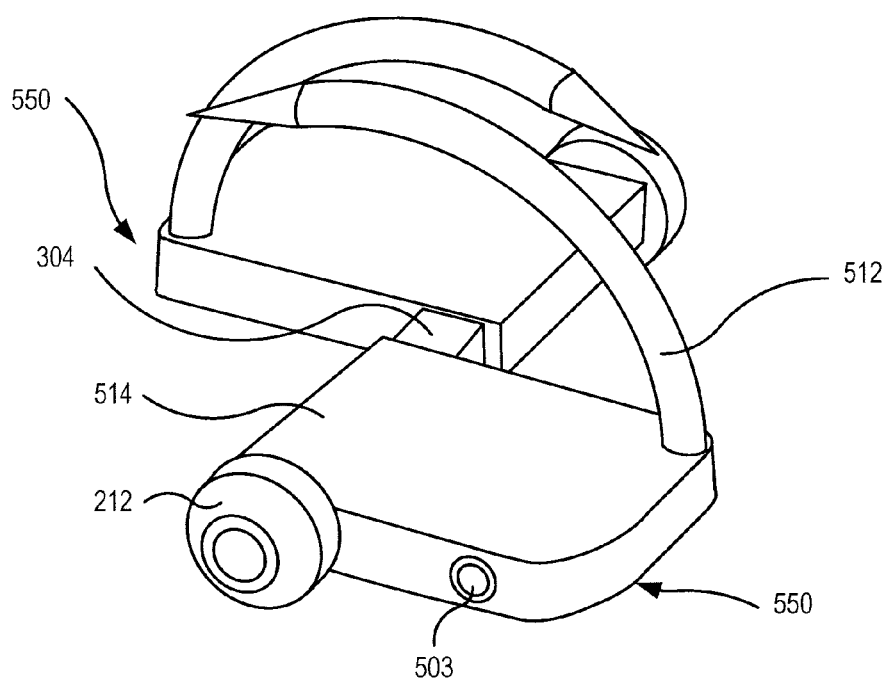
FIG. 18 is a perspective view of two opposing suture face piece assemblies, in an embodiment.

In one RASTER embodiment, with reference to FIG. 18, face half sections 102 are replaced by a RASTER face half section 550 having a suture face 514, or a hook and loop feature (not shown). In a hook and loop embodiment one face half section of each face has hooks and one face half section has loops on a side exposed after transformation. The hooks fixed to a first device 100 interlock with the loops fixed to a second device 100 to mechanically couple the devices 100.

In a RASTER embodiment, suture face 514 may have a hooked suture or needle 512. Optionally, face piece assembly 550 may include a hollow interior and be of adequate size as to act as a reservoir. An optional nozzle 503 is shown integrated with face piece assembly 501. Optional nozzle 503 allows the optional hollow interior of face piece assembly 550 to hold and release a gas or liquid. Alternatively, reservoirs may be located internally to or otherwise integrated with any component of device 100 including face piece assembly 550, and hub assembly 200. Reservoirs may contain antibacterial agents, antimicrobial agents, debriding agents, growth factors, immune cell effector molecules, astringent materials or other therapeutic agents. This embodiment of device 100 may close, monitor, and treat wounds. The movement of face axle assembly 300 (FIG. 11) during inversion of device 100 in combination with the opposing rotations of the face piece assembly 550 (FIG. 18) having attached suture needle 512 may be employed for closing wounds, and interlocking with adjacent devices 100. Each of the six sides of device 100 may have two needles 512. With multiple systems 100 placed in a wound, this configuration allows device 100 to suture the wound closed, binding to skin, while interlocking with adjacent device 100's via needles 512, to form a mechanical bandage of arbitrary size and shape. Furthermore, one or more of a monitoring devices, a wireless receiver, a wireless transmitter, and reservoirs may be included in multiple devices 100. Reservoirs may contain multiple agents or single agents. Reservoirs with different contents may be included in a mixture of devices that form the mechanical bandage. The monitoring devices may monitor properties in the surroundings of device 100. Monitored properties may include pH levels, oxygenation levels, temperature, and hydrostatic pressure. The receiver and transmitter may receive commands and transmit monitored data. The monitoring devices may be used to detect the signature of a specific infectious agent and then signal the release of an appropriate therapeutic agent in response thereto. The monitoring devices may have the ability to detect multiple signals or individual signals. Monitoring devices with different capabilities may be included in a mixture of devices that form the mechanical bandage. The inversion and interlocking of the systems 100 may be synchronously triggered by a timed release trigger, receiving a transmitted signal such as an electromagnetic pulse, exposure to a change is pressure upon deployment from a canister, a temperature change, exposure to a fluid such as blood, or application of a chemical agent. Furthermore, the entire collection of systems 100, monitoring devices and reservoirs may be contained within a hydrogel as a carrier medium. The hydrogel may be a biopolymer or a synthetic polymer containing 90%-99.9% water. The hydrogel carrier may help maintain the proximity of the systems prior to interlocking and may help to seal the wound environment from the external environment. In an embodiment, the hydrogel carrier includes one or more antimicrobial agents to help prevent infection.

FIG. 16 illustrates device 100 in the configuration of FIG. 1 with the two front most face pieces removed to permit viewing of its component parts.

Each face axle assembly 300 is coupled to three rotating arm assemblies 400(1)-(3). Assembly 300 and assembly 400 (1)-(2) are pivotally joined at hinge arm holes 312 (FIG. 11) and rotating arm holes 408 (FIG. 15). The connection mechanism may vary depending on the embodiment.

Rotating arm assembly 400(3) (FIG. 10) is slideably and rotatably engaged with sliding arm 302 (FIG. 8) via pivot hole 404. The movement of rotating arm assembly 400(3) is restricted by the coupled interconnection of assemblies 200, 300, and 400.

In this embodiment, a driving force may be provided by an electric motor 602, (FIG. 16) placed internally to face piece assembly 210 (FIG. 10), as seen through transparent surface 604 (FIG. 16). Electric motor 602 is fixed to the inside of face piece assembly 500 (FIG. 16), and is mechanically engaged with face axle 306 o allow electric motor 602 to cause face piece assembly 210 (FIG. 10) to rotate about face axle 306 (FIG. 11). Due to the coupled interconnection of device 100, electric motor 602 thereby causes the inversion of device 100.

The interconnection of the of the components (hub assembly 200, face axle assembly 300, rotating arm assembly 400, and face piece assembly 210) of device 100 restrict the degrees of freedom to one, meaning that the entire cube inversion movement is coupled, as depicted in FIGS. 1 and 6-9. In the inversion process, each component of device 100 is restricted to follow a single, predetermined path. The specific design and single degree of freedom of the device ensure that there are no collisions or interferences between the components.

FIG. 17 shows one embodiment of a fully expanded device 170, similar to that of FIG. 8, but with the front most two face piece assemblies 210 (FIG. 10) removed to show the internal mechanism as heretofore described.

Section face assemblies 210 are rotatably engaged with face axle 306 (FIG. 11), and form a beveled gear assembly via hinge pivot wheels 308 and face pivot wheels 212. The teeth (not shown) of face pivot wheel 212 intermesh with the teeth (not shown) of hinge pivot wheel 308. Rotation of face axle assembly 300 (detailed above) causes face pivot wheel 212 and hinge pivot wheel 308 to act as a beveled gear, rotating face piece assemblies 210 about face axle 306.

FIG. 19 is a view of a face piece with adjacent components of an embodiment having a single, enlarged, face piece per side of the cubical device.

The singular face piece 702 of FIG. 19 may replace both face half sections 102 of one or more sides of a device as illustrated in FIG. 1. This face piece 702 has three cutouts or slots 704, 706, 708. In this embodiment, a single beveled wheel 710 is present, it serves as an equivalent of face pivot wheel 212 as previously discussed with reference to FIG. 10, and is located within a slot 708. An axle 712 is driven through face piece 702 and serves as an equivalent of face axle 306 to engage a hinge pivot wheel 714 that serves as an equivalent of hinge pivot wheel 308, and attached to the end of hinge arm 716. A coupling element 720 is pivoted in the end of hinge arm 716 and has a hole through which axle 712 passes. A sliding arm 722 serves as an equivalent of sliding arm 302 and has a hole through which axle 712 passes, forming a junction within another slot 706. At an end of face piece 702 opposite that of slot 708 is slot 704 where a coupling element 724 engages axle 712. Coupling element 724 is pivotably engaged within an end of a second hinge arm 726.

Operation of an embodiment having face pieces resembling those of FIG. 19 is similar to that heretofore described with reference to the embodiment of FIG. 1. Initially, hinge arms 716, 726, and sliding arm 722 are perpendicular to a first face of face piece 702. During inversion the face piece 702 extends outwards and rotates such that unslotted edge 728 extends away from the device, while the hinge arms 726, 716 and sliding arm 722 pass through slots 704, 706, 708 with the face piece 702 as shown in FIG. 19. As the rotation completes to the inverted condition, hinge anus 726, 716, and sliding arm 722 become perpendicular to an opposite side of face piece 702. This embodiment is operable with a hub assembly similar to those previously discussed with reference to FIGS. 13 and 14.

FIG. 20 is a perspective view of an embodiment 800 of the cubical device having face pieces 802 that elevate, and then rotate to invert. In this embodiment, face pieces 802 has a side 804 that is exposed to its exterior. Each face piece 802 has a second side 806 that is difficult to see in FIG. 20 but is visible in FIG. 21 where the device 800 has opened, and on FIG. 22 where the face piece assembly is viewed separately from the rest of the device. Each face piece 802 is attached to a mechanism for inverting the face pieces.

Figure 21:
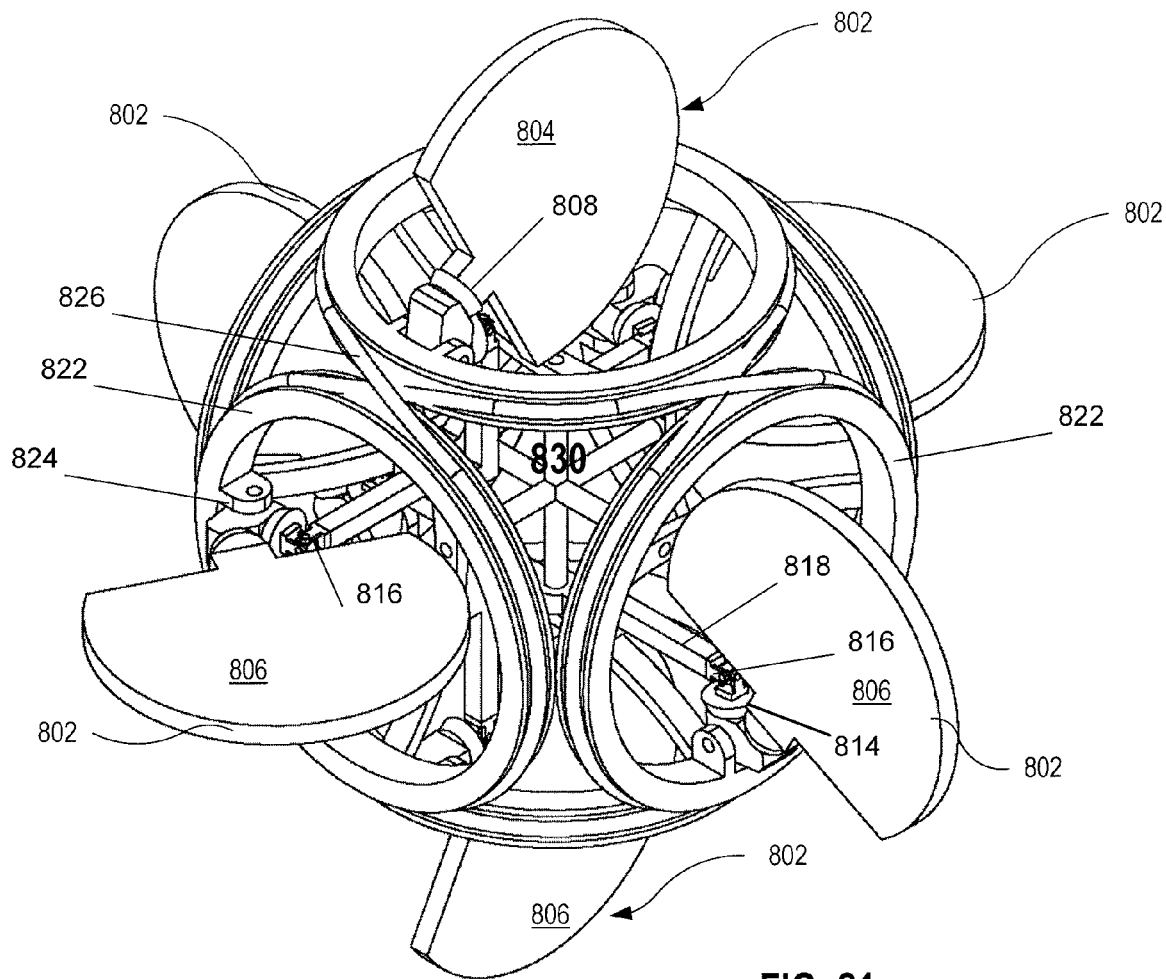
FIG. 21 is an illustration of the embodiment of FIG. 20 midway through an inversion.
Figure 24:
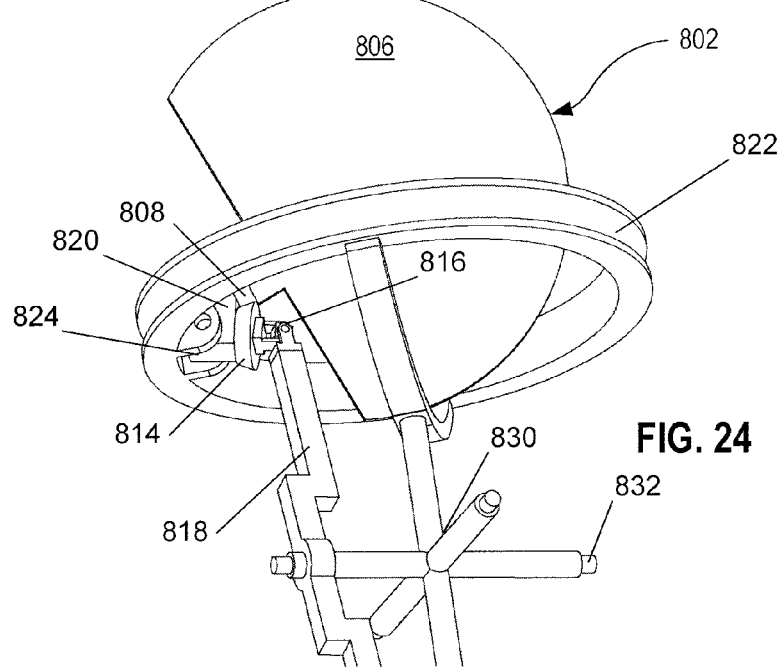
FIG. 24 is a perspective view of the mechanism for elevating and rotating face pieces of the embodiment of FIG. 20.
Figure 25:
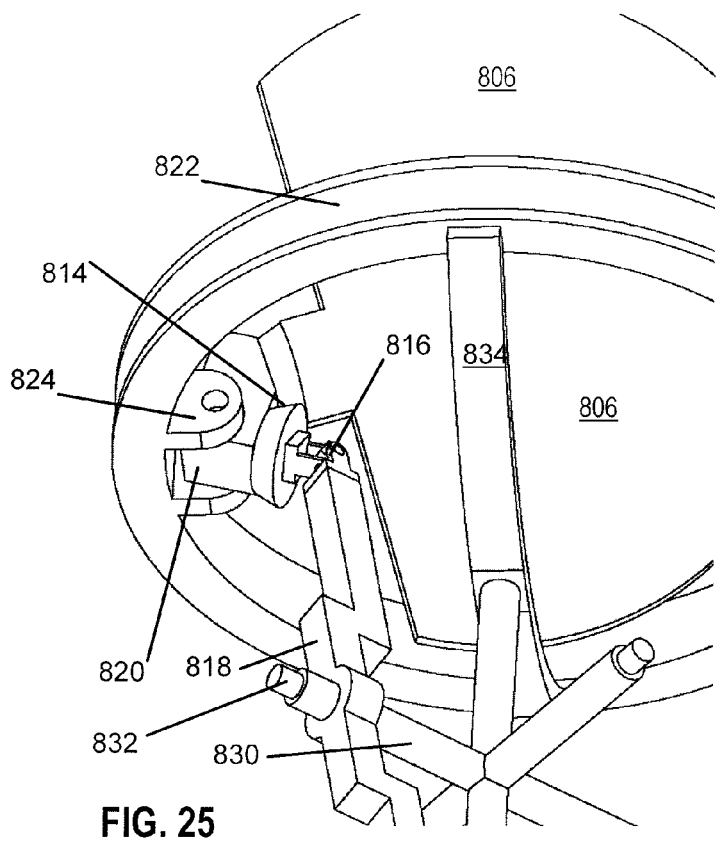
FIG. 25 is an enlarged view of a portion of FIG. 24, provided so details of component parts can be seen.
Figure 26:
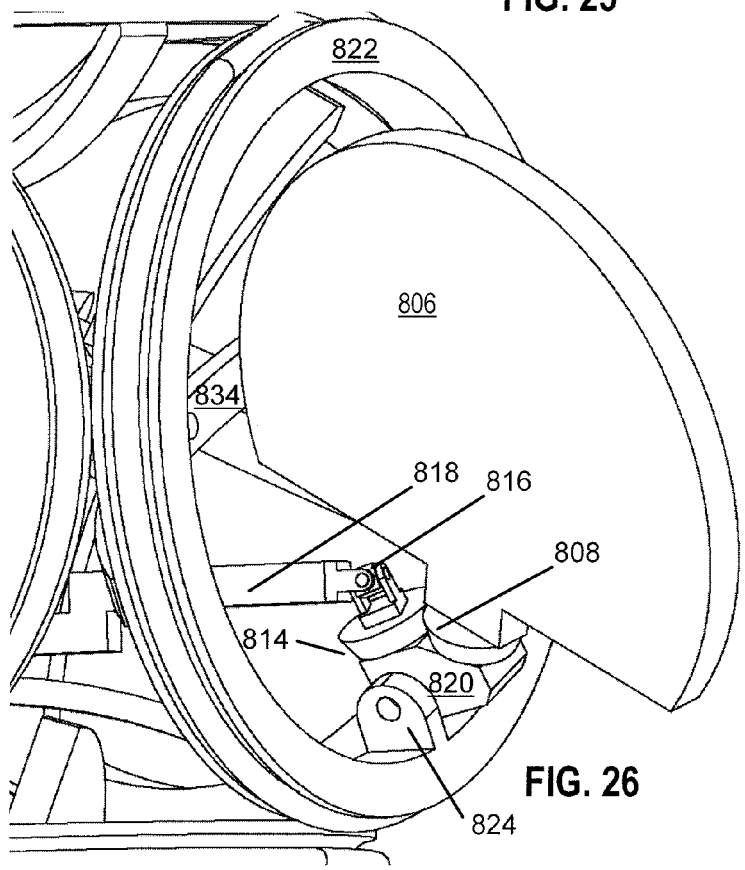
FIG. 26 is an enlarged view of a portion of FIG. 21, provided so details of component parts can be seen.

FIG. 21 is an illustration of the embodiment of FIG. 20 at about one-third of the way through an inversion. FIG. 22 is an illustration of a single face piece assembly of the embodiment of FIG. 20. Face piece assembly 803 has a face piece 802 with its attached beveled driving wheel 808. Driving wheel 808 is rotationally fixed to face piece 802 and has a beveled edge 810, and a face axle 812. Beveled edge 810 may have a friction surface, a textured surface, or bevel-gear teeth to better engage a beveled surface of a driving wheel 814 (FIG. 21, FIGS. 24, and 25). Driving wheel 814 is attached by a universal joint 816 to a rotating arm 818 and thereby rotationally coupled to the rotating min 818. In alternative embodiments, the universal joint 816 may be replaced by a flexible coupling such as a section of elastomeric tubing or a coil spring.

A hinged link 820 is provided for each face piece 802. Link 820 has a bearing for retaining the face axle 812 (FIG. 22) of the face piece. Link 820 is also hinged to ears 824 attached to the pulley 822 associated with the face piece.

FIG. 23 is an illustration of a serpentine belt 826 that may be used in an embodiment to run over pulleys 822 and couple inversion of multiple sides of the embodiment of FIG. 20, where serpentine belt 826 may also be seen. Either one serpentine belt 826 or two such belts may be used. If one belt 826 is used, motions coupled by the belt 826 on three sides of the device are coupled through rotating arms 818 to the remaining three sides of the device.

A six-armed star-axle 830 is provided, having its center in the center of the device. Each arm of the star-axle 830 has a bearing surface 832 that serves as a center axle for an associated pulley 822; in the embodiment illustrated the associated pulley 822 has a crossing bow 834 that engages with the bearing surface 832. Each arm of the star-axle 830 also engages with a rotating arm 818. Rotating arm 818 resembles rotating arm 400 of the previously described embodiment of FIGS. 1 and 15 except that it has universal joints 816 at its ends instead of being pinned to hinge plates 316 of hinge arms 310.

In the embodiment of FIG. 20, a rotary motion imparted to any one pulley 822 in an appropriate direction causes rotating arm 818 to become more nearly parallel with an aim of star-axle 830. As it does so, the rotating arm 818 presses outwardly on link 820 through universal joint 816 and wheel 814. This causes link 820 to rotate, tipping outwards. Since face axle 812 (FIG. 22) is inserted into link 820 (FIG. 25), this causes face axle 812 to tip outwards, raising face piece 802 such that rotation of face piece 802 is possible.

Once face piece 802 has risen sufficiently to clear underlying components of the device, as the pulley 822 continues to rotate, pulley 822 effectively rotates about rotating arm 818 because rotating arm 818 is constrained by its interaction with star-axle 830. This causes wheel 814 to rotate one half turn with respect to pulley 822. This in turn causes wheel 814 to rotate driving wheel 808 with which it is engaged, thereby rotating the face piece 802 to conceal the initially exposed side 804 and reveal initially concealed side 806. As the pulley 822 rotates into its final post-inversion position, rotating arm 818 pulls link 820 back towards the center of the device, thereby levering the face-piece 802 back into position on the pulley.

The motions as described are fully reversible, unless an inherently irreversible actuator such as a chemical gas-generator and piston is used. By twisting a pulley 822 in the direction opposite its motion during an initial inversion, a complementary inversion of face piece 802 takes place; revealing side 802 and concealing side 804.

The embodiments of FIG. 20-27 may be motorized. In an embodiment, a motor is placed at the junction of crosspiece 834 with an arm of star axle 830. This motor then serves to rotate the pulley 822 attached to that arm, and, through belt 826, other pulleys 822 of the device. As heretofore stated, rotating a pulley 822 is sufficient to invert all faces of the device.

An alternative actuating device may be a linear actuator that shifts position of a rotating arm 818. This in turn applies forces through universal joint 816 and link 820 to rotate the attached pulley 822; once pulley 822 is rotated the device will invert.

In an alternative embodiment, belt 826 may be removed, and solid star-axle 830 is replaced by a geared hub assembly similar to that illustrated in FIGS. 13 and 14. In this embodiment, pulleys 822 need not have an outer surface suitable for interfacing with belts, these become rings not pulleys. In this embodiment, each crosspiece 834 is cemented directly to an axis arm 204(1-6) of the geared hub assembly. Note that the slip-joint illustrated between axis arm 204(1-6) of the hub assembly and sliding arm 302 is not necessary in this embodiment because pulleys 822 do not shift outwardly in position during an inversion.

In an embodiment, as illustrated in FIG. 27, the space to the sides of the ears 824 is filled in with a housing portion 850 so that the face pieces 802 seal when they close. Face edge 802 could seal against ring or pulley 822 when closed. It is also possible to fill the gaps between the pulleys or rings 822. The gaps could be filled with corners or rounds. There is space for a cubic frame, such as may contain reservoirs, sensors, or other devices, just inside or outside of the pulleys. If the frame is placed to the inside of the pulleys, it is possible to have a slidable seal between the frame and the bottom of the pulleys 822. In an embodiment, the belt is entirely outside of the frame and does not penetrate the seal. In this embodiment the interior of the mechanism is sealed from the outside environment until opened.

Figure 28:
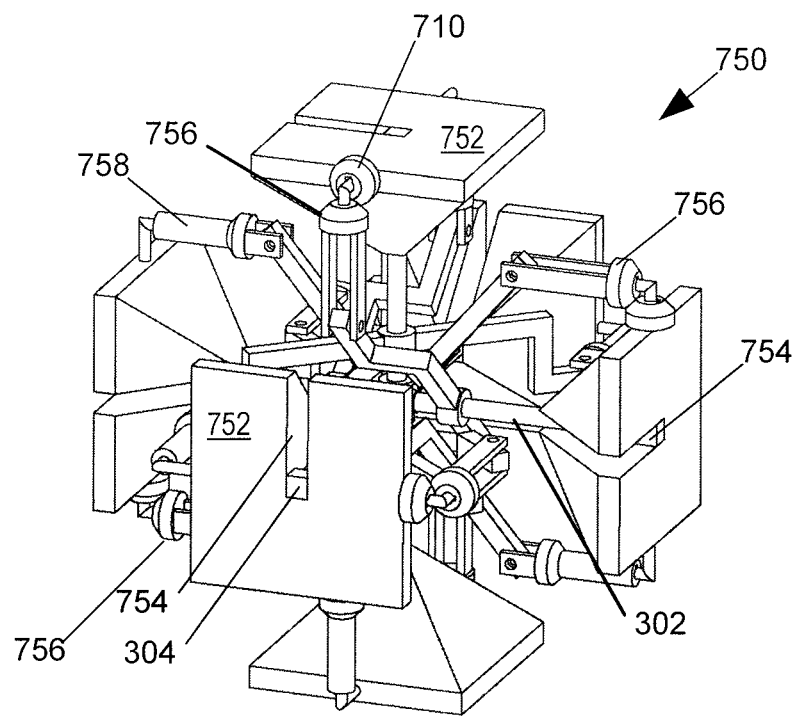
FIG. 28 is a view of a version of the device having single face pieces per side.

The embodiment 750 of FIG. 28 has a mechanism similar to that of FIG. 1 but has single face pieces 752 per side instead of two face piece half sections, with the mechanism modified in a manner similar to that depicted in FIG. 19. Slots 754 are provided to allow face pieces 752 to evert and rotate without interfering with sliding arm 302 or junction 304 of a face axle assembly as previously described. Each face piece 752 is equipped with one driving face pivot wheel 710, which is driven by a hinge pivot wheel 756 as previously described. Each face piece 752 has an undriven side lacking both face pivot wheel and hinge pivot wheel; the undriven side has instead a sleeve bearing fitting 758 replacing the hinge pivot wheel.

Changes may be made in the above methods and systems without departing from the scope hereof. It should thus be noted that the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall therebetween.

What is claimed is:

1. A device 100 having at least two faces, the device being capable of inverting at least two of its faces, the device comprising:
   a hub assembly 200 having a plurality of axis arms 204;
   a plurality of face axle assemblies 300, each face axle assembly having a face axle 306; each of face axle assembly 300 being slidably engaged with an axis arm 204 of the hub assembly 200;
   a plurality of rotating arm assemblies 400, each rotating arm assembly 400 being rotatably engaged with a face axle assembly 300; and
   a plurality of face piece assemblies 210, each face piece assembly 210 having a face piece 102, 702, 802 having a first face 104, 110, 112, 108, 804 and a second face 106, 110, 120, 514, 806;

wherein each face axle assembly 300 is pivotably coupled with two rotating arm assemblies 400 of the plurality of rotating arm assemblies 400, each rotating arm assembly 400 is slideably and rotatably engaged with one face axle assembly of the plurality of face axle assemblies 300, and pivotably coupled with two face axle assemblies of the plurality of face axle assemblies 300, and each face piece assembly 210 of the plurality of face piece assemblies is rotationally engaged with one face axle assembly 300, and wherein the hub assembly 200, face axle assemblies 300, rotating arm assemblies 400, and face piece assemblies 210 are cooperatively configured to extend face pieces 102, 702, 802 outwardly from the device 100, to invert the face pieces 102, 702, 802 and retract the face pieces 102, 702, 802.

2. The device of claim 1 wherein at least one face of the device has two face pieces 102 that rotate in opposite directions about a common axis during inversion.

3. The device of claim 1 wherein at least one face has a single face piece 702 that rotates about face axle 306 during inversion.

4. The device of claim 1, wherein the face axle assembly 300 further comprises a sliding arm 302, at least one face axle 306, at least one beveled pivot wheels 308, and a hinge arm 310 coupled to the pivot wheels 308.

5. The device of claim 1, wherein at least one of the face axle assemblies 300 is slideably and non-rotatably engaged with at least one of the axis arms 204 of the hub assembly 200, rotatably coupled with at least one face piece assembly 210 via a face axle 306, and engaged with a first and a second rotating arm assembly of the plurality of rotating arm assemblies 400.

6. The device of claim 1, wherein at least one face piece assembly of the plurality of face piece assemblies has at least one attached suture needle.

7. The device of claim 1, wherein at least one of hub assembly, face axle assemblies, rotating arm assemblies, and face piece assemblies, supports at least one monitoring device.

8. The device of claim 7, further comprising a transmitter coupled to the monitoring device.

9. The device of claim 1, wherein at least one of hub assembly, face axle assemblies, rotating arm assemblies, and face piece assemblies supports one or more reservoirs capable of disgorging its contents.

10. The device of claim 1, further comprising an actuator coupled to be capable of applying a driving force to drive the device through an inversion process.

11. The device of claim 1, wherein at least one of the face piece assemblies 210 supports a solar power collecting apparatus.

12. A device 800 having at least two faces, the device being capable of inverting its faces comprising:
- at least one ring 822;
- a plurality of face piece assemblies 803, each face piece assembly 803 having a face piece 802 rotationally affixed to a beveled driving wheel 808, where each face piece 802 has a first side 804 and a second side 806;
- a second wheel 814 coupled to drive the beveled driving wheel 808; and
- a rotating arm 818 rotationally coupled to the driving wheel, the rotating arm coupled to a hub assembly 830;
- wherein the ring 822 has a face piece assembly 803 and a link 820 associated therewith, the link being hinged to the ring, and the face piece assembly 803 being coupled to the link in manner such that face piece assembly 803 may rotate relative to the link; and
- wherein rotation of the ring 822 causes rotating arm 818 to rotate thereby causing rotating arm 818 to deflect link 820 thereby deflecting face piece assembly 803; and
- whereby rotation of the ring 822 causes rotating arm 818 to rotate the second wheel 814 thereby rotating driving wheel 808 and rotating face piece assembly 803.

13. The device of claim 12 wherein the hub assembly 830 comprises a star axle.

14. The device of claim 1 or claim 13, wherein the rotating arm comprises a central pivot, and a pair of stepped rotating arms.

15. A device of claim 1 or claim 12, wherein the hub assembly is comprised of at least three beveled transmission wheels, each beveled transmission wheel rotationally fixed to a central axis, an axis of rotation of each beveled transmission wheel situated at an angle to the axis of rotation of two other beveled transmission wheels, and at least two axis arms rotationally fixed to each of at least two bevel transmission wheels and extending along an axis of rotation of the beveled transmission wheels.

16. The device of claim 15, wherein the at least three beveled transmission wheels are selected from the group consisting of beveled gear wheels and beveled frictional surface wheels.

17. The device of claim 12, further comprising an actuator coupled to be capable of applying a driving force to drive the device through an inversion process.

18. The device of claim 12, wherein at least one of hub assembly, rotating arm, and face piece assemblies supports one or more reservoirs capable of disgorging its contents.

19. The device of claim 12 wherein at least one of hub assembly, rotating arm, and face piece assemblies, supports at least one monitoring device.

20. The device of claim 12, wherein at least one face piece assembly of the plurality of face piece assemblies has at least one attached suture needle.

* * * * *